United States Patent [19]

Williamson et al.

[11] Patent Number: 5,246,971
[45] Date of Patent: Sep. 21, 1993

[54] METHOD OF INHIBITING NITRIC OXIDE FORMATION

[75] Inventors: Joseph R. Williamson, Town and Country; John A. Corbett, St. Louis; Michael L. McDaniel, Glendale; Ronald G. Tilton, St. Louis, all of Mo.

[73] Assignee: Washington University, St. Louis, Mo.

[21] Appl. No.: 843,387

[22] Filed: Feb. 28, 1992

Related U.S. Application Data

[63] Continuation-in-part of Ser. No. 807,912, Dec. 16, 1991, abandoned.

[51] Int. Cl.⁵ .............................. A61K 31/155
[52] U.S. Cl. ................... 514/634; 514/866
[58] Field of Search ............. 514/634, 866; 564/238

[56] References Cited

U.S. PATENT DOCUMENTS 4,758,583 7/1988 Cerami et al. ............... 514/399
4,983,604 1/1991 Ulrich et al. ............... 514/238.5

FOREIGN PATENT DOCUMENTS 450598 10/1991 European Pat. Off. .

OTHER PUBLICATIONS

Bredt et al., Nature 351, 714-718 (1991).
Moncada et al., Pharmacol. Rev. 43, 109-142 (1991).
Brownlee et al., Science 232, 1629-1632 (1986).
Bucala et al, J. Clin, Invest. 87, 432≧438 (1991).
Tilton et al. Invest. Ophthalmol. Vis. Sci. 31, 342 (1990).
Wiliamson et al., Diabetes & Metabolisme 16, 369-370 (1990).
Chang et al., Diabetes 40 (Supp. 1) 210A (1991).
Corbett et al., J. Biol. Chem. 266, 21351-21354 (1991).
Chem. Absts. 115: 248104, Griffith WO 91 04,023 (1991).

Primary Examiner—Frederick E. Waddell
Assistant Examiner—Raymond J. Henley, III
Attorney, Agent, or Firm—Scott J. Meyer

[57] ABSTRACT

A method is disclosed for inhibiting nitric oxide formation in a warm blooded mammal which comprises administering to said mammal an effective nitric oxide inhibitory amount of methylguanidine or dimethylguanidine.

5 Claims, 4 Drawing Sheets

METHOD OF INHIBITING NITRIC OXIDE FORMATION

ACKNOWLEDGEMENT OF GOVERNMENT SUPPORT

This work was supported in part by National Institutes of Health grants KD06181, T32 DK07296, EY06600, HL39934, and DK20579.

CROSS-REFERENCE TO RELATED APPLICATION

This is a continuation-in-part of application Ser. No. 07/807,912, filed Dec. 16, 1991, now abandoned.

BACKGROUND OF THE INVENTION

This invention relates to a method of inhibiting nitric oxide formation in warm blooded mammals and, more particularly, to the administration of methylguanidine or dimethylguanidine as an inhibitor of nitric oxide production.

Nitric oxide synthase catalyzes the mixed functional oxidation of L-arginine to L-citrulline and nitric oxide (NO., 1,2). NO. appears to function as either a signaling or an effector molecule depending on the isoform of the enzyme. The constitutive isoform of nitric oxide synthase produces small amounts of NO. which activate guanylate cyclase resulting in the formation of cGMP which mediates endothelium-dependent relaxation (2) and neural transmission (3). NO. is produced in much larger amounts by the cytokine and endotoxin inducible isoform of nitric oxide synthase, and in macrophages functions as an effector molecule which appears to mediate the cytotoxic actions of macrophages on target cells (4). Since NO. is a potent vasodilator and increases blood flow, and since vasoactive agents (such as histamine and bradykinin), which stimulate NO. production increase both blood flow and vascular permeability, NO. may be a candidate for mediating increases in blood flow and vascular permeability induced by diabetes and elevated glucose (5).

Recently, Interleukin-1 (IL-1) has been shown to induce the expression of the cytokine inducible isoform of nitric oxide synthase in pancreatic islets. The production of NO. has been proposed to be the effector molecule which mediates IL-1's inhibitory affects on islet function (6,7). Generation of an IL-1-induced EPR detectable iron-nitrosyl complex, which is prevented by $N^G$-monomethyl-L-arginine (NMMA), has been used to confirm the formation of nitric oxide by islets (8). Also, the protein synthesis inhibitor, cycloheximide, has been shown to block IL-1-induced nitrite formation, cGMP accumulation, and EPR detectable iron-nitrosyl complex formation by islets, thus establishing that IL-1 induces the cytokine inducible isoform of nitric oxide synthase in pancreatic islets (7).

The pathogenesis of diabetic complications has been linked to imbalances in sorbitol, mvo-inositol, and 1,2-diacyl-sn-glycerol metabolism, and to non-enzymatic glycation of cellular and extracellular constituents (5). The glycation link is supported by evidence that aminoguanidine, a nucleophilic hydrazine compound, interferes with the formation of these glycation products and also attenuates the development of several diabetes-induced vascular (5,9), neural (10), and collagen changes (11). Bucala et al. (12) recently reported that quenching of NO. in vitro by glycated albumin is attenuated by aminoguanidine (present during exposure of albumin to glycating agents) and suggested that glycation products may impair endothelium-dependent relaxation by attenuating NO. activity.

BRIEF DESCRIPTION OF THE INVENTION

In accordance with the present invention a novel method of inhibiting nitric oxide formation in warm blooded mammals is provided. The method comprises administering to a warm blooded mammal a small but effective amount of methylguanidine or dimethylguanidine to inhibit nitric oxide production.

It will be understood that pharmaceutically acceptable salts of these compounds, e.g. the HCl and sulfate salts, also can be administered to the mammal.

At the present time the pathogenesis of diabetic complications remains obscure and there is no known medication which has been shown to prevent them. Although diabetic complications are strongly linked to severity of diabetes as reflected by blood sugar levels and glycated hemoglobin, the efficacy of attempts to prevent and/or reverse diabetic complications by efforts to normalize blood sugar levels remains to be documented.

In applicant's copending application Ser. No. 07/807,912, filed Dec. 16, 1991, a method is disclosed whereby aminoguanidine is administered to a warm blooded mammal at doses which inhibit nitric oxide production without producing a substantial elevation in arterial blood pressure. In accordance with the present invention, it has been found that methylguanidine is a potent inhibitor of constitutive and cytokine-induced NO production as manifested by increases in arterial blood pressure when injected intravenously in normal rats. However, in contrast to aminoguanidine, methylguanidine is relatively ineffective in preventing glucose-induced advanced glycation products manifested by the development of fluorescence products characteristic of advanced glycation end products. Thus, it is evident that the prevention by methylguanidine of diabetesinduced vascular dysfunction is attributable to its ability to block NO production rather than blocking advanced glycation end product formation.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which briefly:

Figure 1:
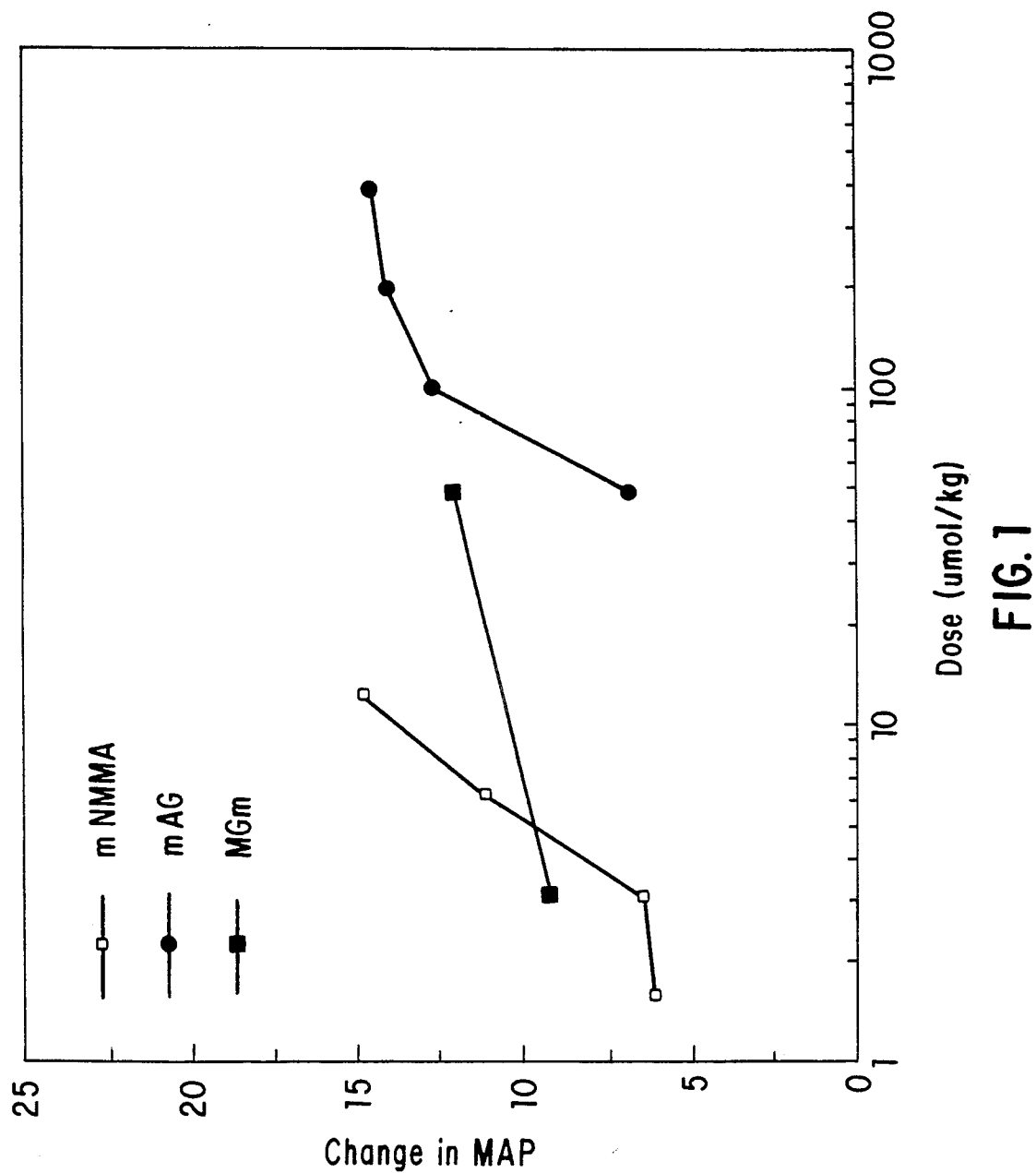
FIG. 1 is a graphical representation which shows the changes in mean arterial blood pressure (MAP) induced by bolus intravenous injections of methylguanidine (MG), aminoguanidine (AG) or $N^G$-monomethyl-L-arginine (NMMA) in which change in MAP is recorded in % increase in pressure above baseline and the dose of the bolus injection is recorded in μmol/kg.

Effects of methylguanidine on constitutive (vascular) nitric oxide synthase activity were assessed by monitoring mean arterial blood pressure (MAP) changes following intravenous injection of methylguanidine in anesthetized, normal rats. The dose responses of methylguanidine, aminoguanidine and NMMA are shown in FIG. 1.

Figure 2:
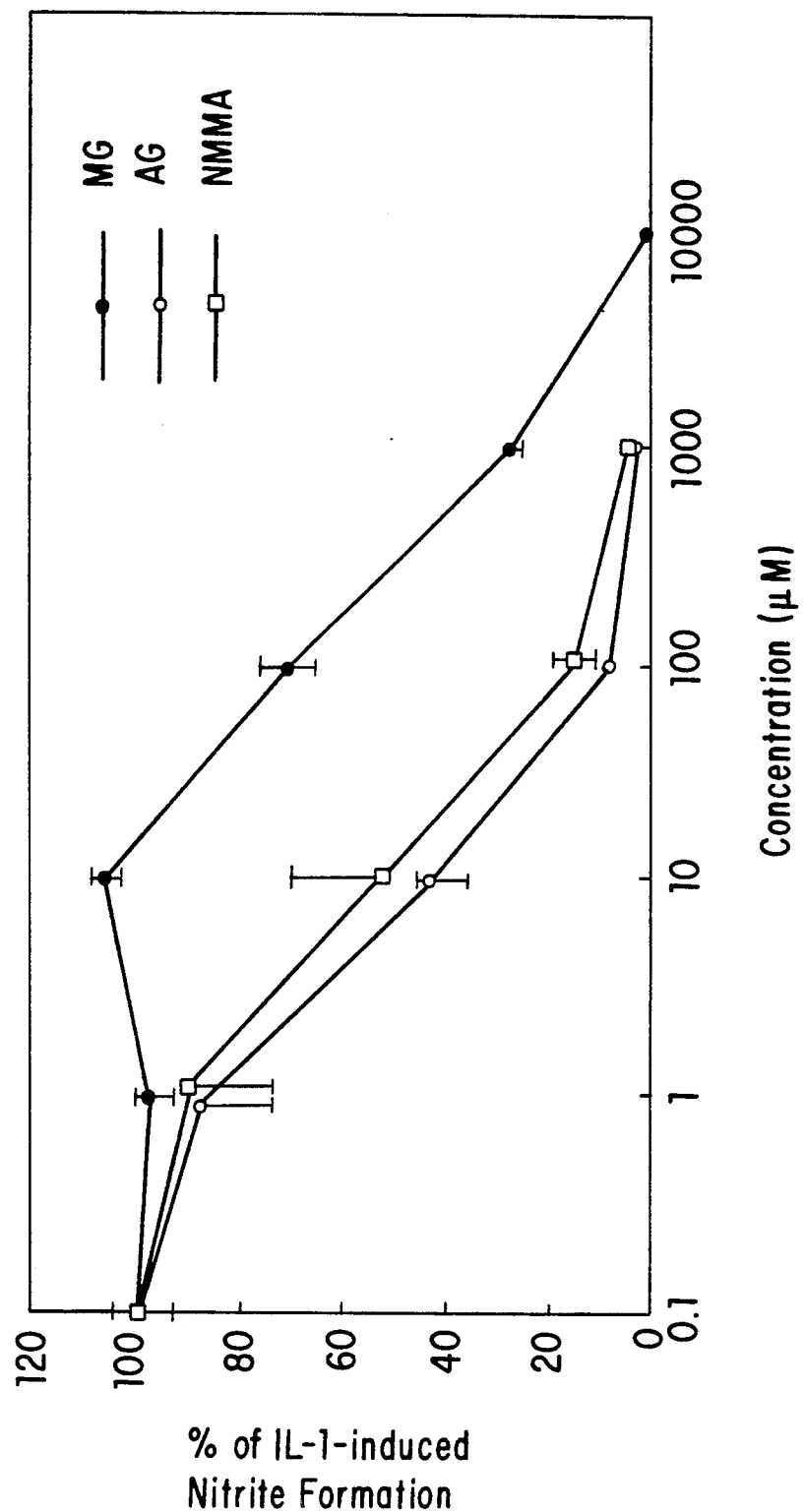
FIG. 2 is a graphical representation which shows the effects of methylguanidine (MG), aminoguanidine (AG) or $N^G$-monomethyl-L-arginine (NMMA) on IL-1-induced nitrite formation by Rin-m5F cells in which the effect on nitrite formation is recorded in % of IL-1βB-induced nitrite formation and the concentration of the test compounds is recorded in μM.
Figure 3:
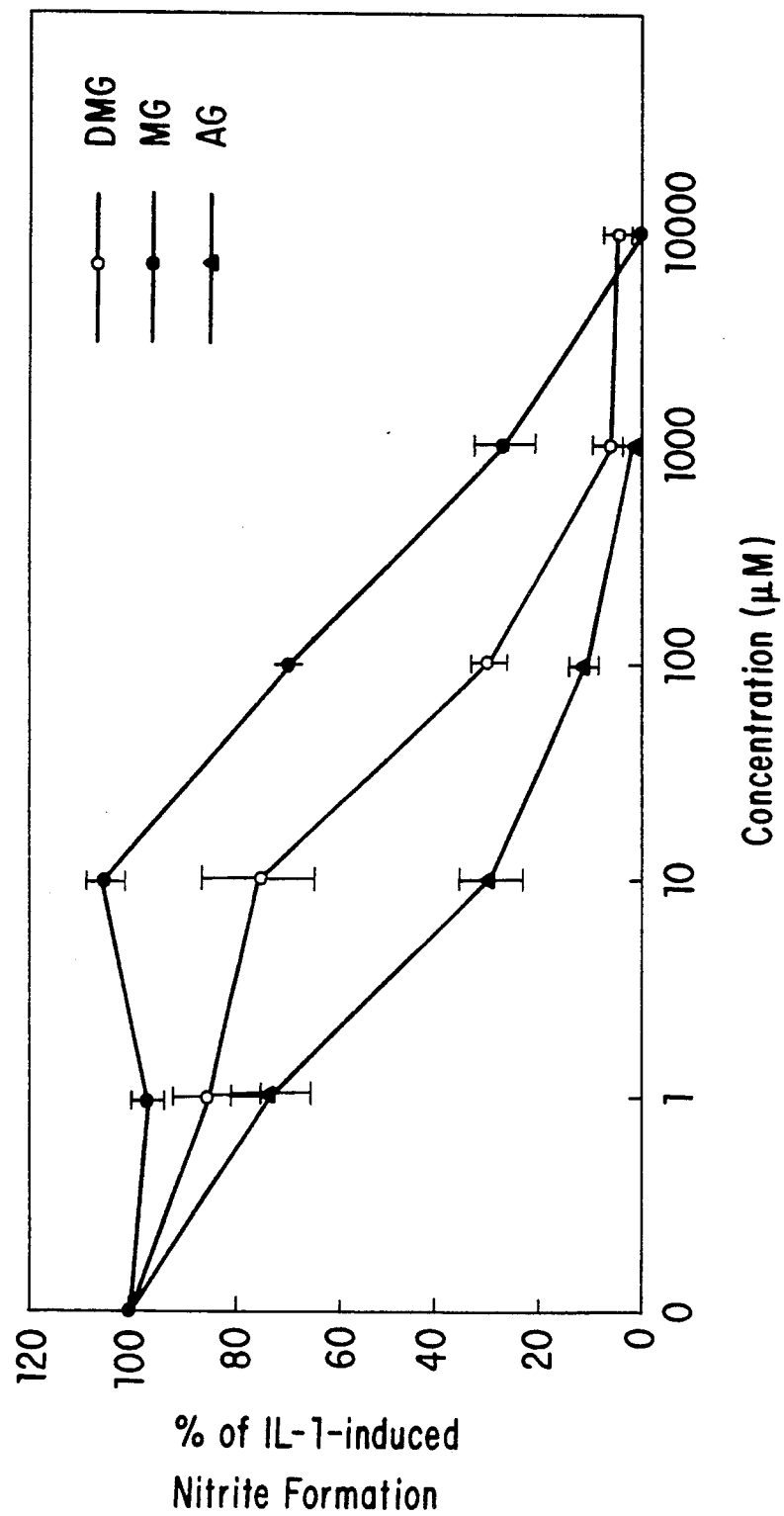
FIG. 3 is a graphical representation which shows the effects of methylguanidine (MG), dimethylguanidine (DMG) and aminoguanidine (AG) on IL-1β-induced nitrite formation by Rin-m5F cells as in FIG. 2.

Since methylguanidine contains strong structural similarities to L-arginine and the competitive inhibitor of nitric oxide synthase, viz. NMMA, in that these compounds contain two chemically equivalent guanidine nitrogen groups, the effects of methylguanidine on IL-1β-induced formation of nitrite and cGMP by Rin m5F cells were examined and compared to the effects of NMMA in similar tests (FIG. 2). Also in similar tests, methylguanidine and its close analog, dimethylguanidine, were each compared to the effects of aminoguanidine (AG) (FIG. 3). The Rin m5F cell line is an insulinoma cell line of the rodent β-cell that has been shown to contain the cytokine-inducible isoform of nitric oxide synthase. FIGS. 2 and 3 demonstrate the dose response of methylguanidine, dimethylguanidine, aminoguanidine and NMMA or AG on IL-1β-induced formation of nitrite (an oxidation product of nitric oxide) from Rin m5F cells incubated for 18 hrs with 5 units/ml IL-1β± the indicated concentrations of methylguanidine, dimethylguanidine, aminoguanidine and NMMA or AG.

Figure 4:
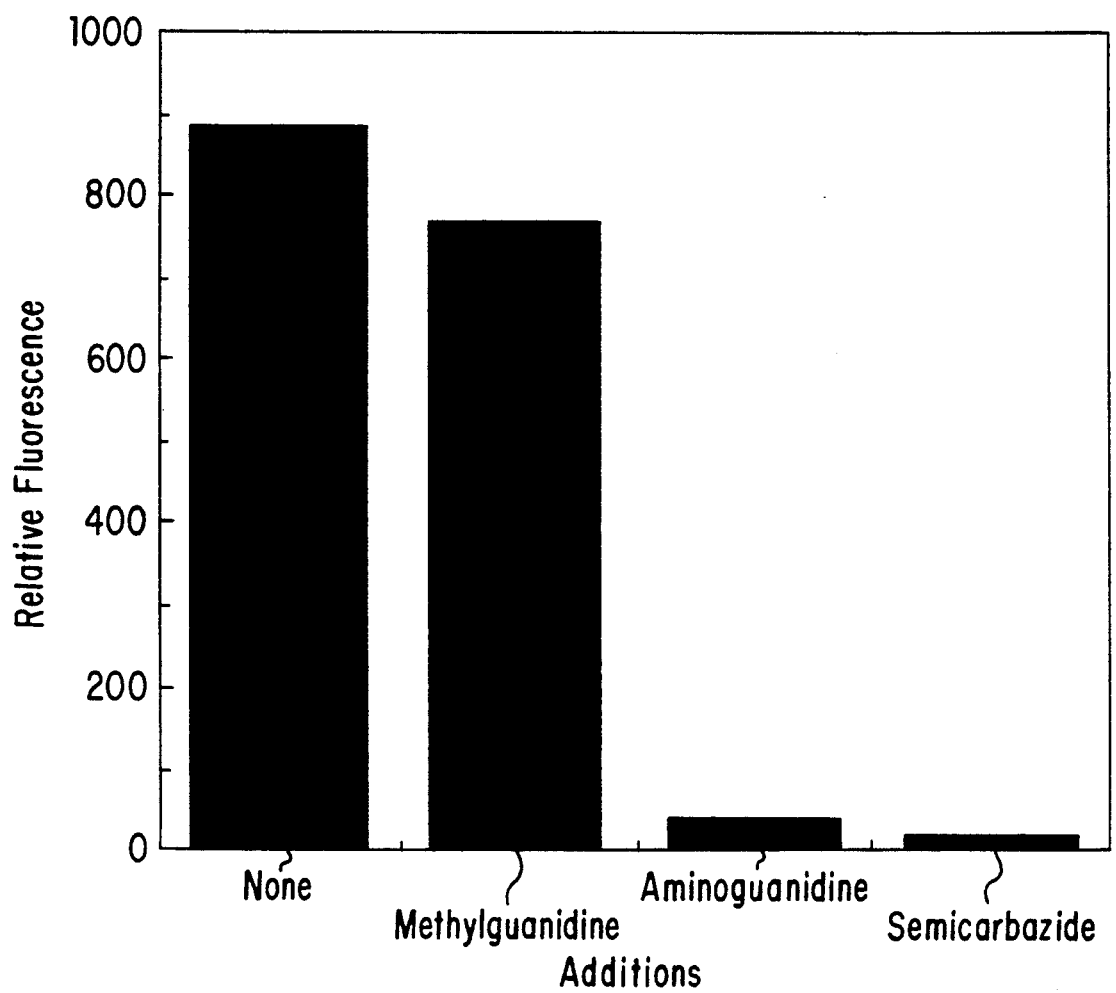
FIG. 4 is a bar chart which shows the relative development of fluorescence products upon incubation of methylguanidine, aminoguanidine or semicarbazide in glucose-6-phosphate/lysine (G-6-P/Lysine) for six days.

The effects of methylguanidine on glycation were assessed by measuring the development of fluorescence products upon its incubation in glucose-6-phosphate/lysine and compared to the corresponding effects of aminoguanidine and semicarbazide. The results are shown in FIG. 4 and indicate that methylguanidine is relatively ineffective (compared to aminoguanidine and semicarbazide) in preventing glucose-induced glycation products as manifested by the development of fluorescence products which are characteristic of glycation end products.

In order to further illustrate the invention, the following detailed EXAMPLES were carried out although it should be understood that the invention is not limited to these specific EXAMPLES or the details described therein. The results obtained in these EXAMPLES are shown in Tables 1 to 5 and the accompanying FIGS. 1 to 4.

EXAMPLE I

This example illustrates a method to prevent diabetes-induced vascular dysfunction using methylguanidine to inhibit nitric oxide synthase.

MATERIALS AND METHODS

Animal Protocols

All rats used in these tests were housed and cared for in accordance with the guidelines of the University Committee for the Humane Care of Laboratory Animals and in accordance with NIH guidelines on laboratory animal welfare. Rats were housed individually, allowed food (standard rat chow; Ralston Purina, Richmond, IN) and water *ad libitum*, and were on a 12 hour light/dark cycle. Male, Sprague-Dawley rats initially weighing 225-250 g were divided into four groups: group 1, untreated controls; group 2, methylguanidine (mg)-treated controls; group 3, untreated diabetics; and group 4, mg-treated diabetics. Diabetes was induced by intravenous injection of 45 mg/kg body weight streptozotocin (Sigma Chemical Co., St. Louis, MO) using ketamine anesthesia. Methylguanidine hydrochloride (Sigma Chemical Co.) was administered subcutaneously once daily at a dose of 25 mg/kg body weight. In addition, control rats were given water containing 2.5 g/L methylguanidine while diabetic rats were given water containing 1 g/L. Water consumption was monitored weekly for all rats.

Body weights were measured weekly, nonfasting morning plasma glucose levels were assessed 3 days after injection of streptozotocin (to ensure induction of diabetes), then biweekly thereafter using the conventional glucose oxidase method of Lowry and Passoneau (14). After 4 weeks, all rats were placed into individual metabolic cages for 24 hours to determine food consumption (g/100 g body weight/24 hr) and urine output (ml/kidney/24 hr). A sample of urine was stored at −70° C. for determination of urinary albumin excretion (see below). Five weeks after induction of diabetes, rats were used for the permeability and blood flow studies detailed below.

Test Protocol

Regional vascular albumin permeation was quantified by use of an isotope dilution technique based on the injection of bovine serum albumin (BSA) labeled with 2 different iodine isotopes, $^{131}$I and $^{125}$I (15-17). $^{125}$I-BSA was used to quantify vascular albumin filtration after 10 min of tracer circulation, while $^{131}$I-BSA served as a plasma volume marker for correction of $^{125}$I-BSA tissue activity for tracer contained within vessels.

Preparation of radiolabeled tracers. Purified monomer BSA (20 mg) was iodinated with 1 mCi of $^{131}$I or $^{125}$I (NEN Research Products, Boston, MA) by the iodogen method as previously described (15). $^{57}$Co-EDTA was prepared as previously described (15, 16) and $^{46}$Sc-microspheres (10 μm diameter) were used to assess regional blood flow as detailed below.

Surgical Procedures. Rats were anesthetized with inactin (Byk Gulden, Konstanz, FRG) (∼100 mg/kg body weight injected i.p.), and core body temperature maintained at 37±0.5° C. using heat lamps, a 37° C. surgical tray, and a rectal temperature probe. The left femoral vein, left iliac artery, right subclavian artery, and right carotid artery were cannulated with polyethylene tubing (0.58 mm i.d.) filled with heparinized saline (400 U heparin/ml). The femoral vein cannula was used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of 0.055 ml/min. The tip of the cannula in the right carotid artery was placed in the left ventricle of the heart and was used for injection of radiolabeled microspheres. The trachea was intubated and connected to a small rodent respirator for continuous ventilatory support.

Test Procedure

At time 0, $^{125}$I-albumin (in 0.3 ml of saline) and $^{57}$Co-EDTA (~0.1μCi in 0.1 ml of saline) were injected i.v. and the withdrawal pump was started simultaneously. Eight min after time 0, 0.2 ml of $^{131}$I-BSA was injected and 1 min later, the 46Sc-microspheres were injected slowly over ~30 sec. At the 10 min mark, the heart was excised to stop all blood flow, the withdrawal pump was stopped simultaneously, and various tissues were sampled for gamma spectrometry.

Both kidneys, bladder, and connecting ureters were removed. Eyes were dissected as previously described (15, 16) and tissues from both eyes were pooled prior to gamma spectrometry. All tissue samples and arterial plasma samples were weighed, then counted in a gamma spectrometer interfaced with a Hewlett-Packard 1000A computer in which the data were corrected for background and stored for subsequent analysis.

Data Analysis

A quantitative index of $^{125}$I-BSA tissue clearance was calculated as previously described (15, 16, 17) and expressed as μg plasma/g tissue wet weight/min. Very briefly, $^{125}$I-BSA tissue activity was corrected for tracer contained within the tissue by multiplying $^{125}$I-BSA activity in the tissue by the ratio of $^{125}$I-BSA/$^{131}$I-BSA activities in the arterial plasma sample obtained at the end of the test. The vascular-corrected $^{125}$I-BSA tissue activity was divided by the time-averaged $^{125}$I-BSA plasma activity (obtained from a well mixed sample of plasma taken from the withdrawal syringe) and by the tracer circulation time (10 min) and then normalized per g tissue wet weight.

Glomerular filtration fate (GFR) was calculated as previously described (18). To calculate regional blood flows, the total activity of $^{46}$Sc in the retina was divided by the total activity of $^{46}$Sc in the reference blood sample obtained from the withdrawal syringe, then multiplied by the pump withdrawal rate, and expressed as ml/g tissue wet weight per minute (19).

Preparation of advanced glycosylation end products

Lysine-derived advanced glycosylation products were prepared as described by Bucala et al. (12) by incubating 100 mM concentrations of glucose-6-phosphate and L-lysine in 0.2 M sodium phosphate buffer, pH 7.4. The incubations were maintained sterile, and were kept in the dark at room temperature for ~6 days, at which time relative fluorescence was measured as an index of glycation using a Perkin-Elmer LS-5B luminescence spectrometer with excitation at 370 nm and emission at 440 nm. Samples were diluted 1:11 with saline prior to spectrometry. The ability of 10 and 100 mM concentrations of methylguanidine, aminoguanidine, or semicarbazide to inhibit the glycation process was compared in two separate tests (FIG. 4).

Blood Pressure Measurement

Systolic blood pressure was measured at weekly intervals in conscious rats using the tail-cuff method (20, 2). Animals were adapted to the procedure initially by placing them in a restrainer and inflating the sphygmomanometer several times. Blood pressure also was obtained from the iliac artery cannula in anesthetized rats during the permeability studies.

Effects of bolus injections of methylguanidine on mean arterial blood pressure Normal male, Sprague-Dawley rats weighing 250–300 g were anesthetized with 100 mg/kg body weight inactin, followed by 0.1 ml/kg body weight d-tubocurarine chloride, the left femoral vein (for tracer injection) and right iliac artery (for monitoring blood pressure) were cannulated with polyvinyl tubing (0.8×0.5 mm) filled with heparinized saline, and the trachea was cannulated and connected to a small rodent respirator for continuous ventilatory support. Following stabilization of arterial pressure, increasing amounts (3.1 and 50 μmol/kg body weight) of methylguanidine or $N^G$-monomethyl-L-arginine (NMMA) were injected intravenously in a volume of 0.5 ml in separate animals and the peak pressure increase was recorded using a Gould RS 3200 recorder. Results were expressed as a percent increase in pressure above baseline.

Statistical Analysis

Data are expressed as mean ±1SD. An analysis of variance was performed using the SAS general linear models procedure. To reduce potential type 1 errors related to multiple comparisons, overall differences among groups for each parameter were preliminarily assessed by the Van Der Waerden test. If statistically significant differences (at $p<0.05$) were indicated among groups for a given parameter, pair-wise comparisons were assessed by least square means following a nonparametric (rank order) Blom transformation of all data.

EXAMPLE II

This example illustrates the effects of methylguanidine on IL-1β-induced nitrite formation by Rin m5F cells (FIG. 2). Rin m5F cells, obtained from the Washington University Tissue Culture Support Center, were removed from growth flasks (55–80 million cells/flask) by trypsin/EDTA treatment, and aliquoted into 1 ml Petri dishes (1–2 million Rin m5F cells per condition). Cells were incubated for 18 hrs (under an atmosphere of 95% air and 5% $CO_2$) in 1 ml of complete CMRL-1066 tissue culture media (CMRL supplemented with 10% heat-inactivated, fetal bovine serum, 2 mM L-glutamine, 50 units/ml penicillin, and 50 μg/ml streptomycin), or complete CMRL-1066 supplemented with methylguanidine (MG), aminoguanidine (AG) or NMMA. Following incubation, the supernatant was removed and nitrite was determined on 100 μl aliquots by conventional procedures as previously described (8,13). The results are expressed as the % of IL-1 induced nitrite formation, and are the mean ± SEM of 4 individual tests containing 3 replicates per test. The results demonstrate that both AG and NMMA are ~10 fold more potent than MG at inhibiting nitric oxide formation by the cytokine inducible isoform of nitric oxide synthase.

EXAMPLE III

The effects of each of methylguanidine, 1,1-dimethylguanidine and aminoguanidine on IL-1β-induced nitrite formation by Rin m5F cells were tested by the procedures described in EXAMPLE II and the results are shown in FIG. 3. The results demonstrate the following order of potency, AG>DMG>MG, for inhibiting the cytokine inducible isoform of nitric oxide synthase.

Tables 1 to 5, below, and the accompanying FIGS. 1 to 4 record the results obtained in the foregoing EXAMPLES. These results indicate that methylguanidine and dimethylguanidine are potent inhibitors of constitutive and cytokine-induced NO production. This is manifested by increases in mean arterial blood pressure by methylguanidine when injected intravenously in normal rats as shown in FIG. 1 and by inhibition of IL-1β-induced increases in nitrite in rodent insulinoma cells with methylguanidine and dimethylguanidine as shown in FIGS. 2 and 3, respectively. Since methylguanidine is relatively ineffective (in contrast t aminoguanidine) in preventing glucose-induced glycation products (manifested by the development of fluorescence products characteristic of advanced glycation end products (FIG. 4), the prevention by methylguanidine of diabetes-induced vascular dysfunction is believed to be attributable to its ability to block NO production. Methylguanidine and its close analog, dimethylguanidine, thus should be useful for prevention of diabetic complications as well as inflammatory and immunological diseases in which increased NO production is involved.

TABLE 1

Effects of diabetes and methylguanidine on body weights, plasma glucose and water consumption.

|  | control | control + mg | diabetic | diabetic + mg |
|---|---|---|---|---|
| number of rats | 10 | 11 | 14 | 18 |
| body weights (g) | | | | |
| initial | 249 ± 20 | 256 ± 16 | 250 ± 19 | 248 ± 18 |
| week 2 | 326 ± 25 | 300 ± 31 | 297 ± 23 | 271 ± 23 |
| week 4 | 375 ± 41 | 351 ± 37 | 334 ± 45 | 294 ± 50 |
| plasma glucose (mg/dL) | 130 ± 15 | 131 ± 28 | 419 ± 120 | 420 ± 87 |
| hematocrit (%) | 43 ± 2 | 42 ± 1 | 42 ± 1 | 42 ± 2 |
| blood pressure (mm Hg) | | | | |

TABLE 1-continued

Effects of diabetes and methylguanidine on body weights, plasma glucose and water consumption.

|  | control | control + mg | diabetic | diabetic + mg |
|---|---|---|---|---|
| conscious | 125 ± 18 | 121 ± 7 | 123 ± 5 | 126 ± 5 |
| anesthetized | 118 ± 14 | 114 ± 14 | 120 ± 16 | 121 ± 14 |
| water consumption (ml/day) | 46 ± 6 | 32 ± 9 | 108 ± 42 | 93 ± 53 |

TABLE 2

Effects of diabetes and methylguanidine (mg) on $^{125}$I-albumin permeation$^a$

|  | control | control + mg | diabetic | diabetic + mg |
|---|---|---|---|---|
| number of rats | 10 | 8 | 11 | 9 |
| eye | | | | |
| anterior uvea | 266 ± 77$^b$ | 359 ± 146 | 623 ± 109$^a$ | 370 ± 60$^b$ |
| posterior uvea | 328 ± 106 | 312 ± 101 | 742 ± 134$^a$ | 358 ± 108 |
| retina | 47 ± 12 | 61 ± 11 | 116 ± 30$^a$ | 55 ± 18 |
| sciatic nerve | 47 ± 13 | 47 ± 10 | 121 ± 22$^a$ | 50 ± 10 |
| aorta | 62 ± 20 | 60 ± 18 | 155 ± 37$^a$ | 85 ± 41 |
| kidney | 727 ± 239 | 714 ± 214 | 1011 ± 265$^c$ | 738 ± 169 |
| lung | 1805 ± 532 | 1656 ± 454 | 1405 ± 324 | 1,498 ± 487 |
| diaphram | 201 ± 75 | 190 ± 27 | 210 ± 61 | 216 ± 46 |
| heart | 521 ± 135 | 731 ± 269 | 534 ± 62 | 599 ± 68 |
| brain | 5 ± 3 | 4 ± 3 | 5 ± 2 | 6 ± 4 |

$^a$μg plasma/g wet weight/min; see Methods in EXAMPLE I for details of test procedure.
$^b$mean ± SD
Significantly different from untreated controls by Student's t test: $^ap < 0.001$; $^bp < 0.05$; $^cp < 0.01$.

TABLE 3

Effects of diabetes and methylquanidine (mg) on regional blood flows*

|  | (n) | anterior uvea | posterior uvea | retina | sciatic nerve | kidney |
|---|---|---|---|---|---|---|
| control | (10) | 2.0 ± 0.6 | 3.4 ± 0.6 | 0.43 ± 0.02 | 0.06 ± 0.02 | 6.5 ± 0.3 |
| control + mg | (8) | 2.4 ± 0.5 | 3.3 ± 0.6 | 0.45 ± 0.07 | 0.07 ± 0.03 | 4.8 ± 0.3$^a$ |
| diabetic | (10) | 2.7 ± 0.3$^b$ | 4.2 ± 0.5$^b$ | 0.57 ± 0.08$^a$ | 0.09 ± 0.01$^a$ | 6.0 ± 0.4$^c$ |
| diabetic + mg | (9) | 2.3 ± 0.6 | 3.9 ± 0.6 | 0.45 ± 0.04 | 0.06 ± 0.02 | 5.8 ± 0.3$^a$ |

*ml/min/g wet weight; values are mean ± 1SD measured using radiolabeled microspheres (~10 μm diameter)
Significantly different from controls by Student's t test: $^ap < 0.001$; $^bp < 0.005$; $^cp < 0.01$

TABLE 4

Effects of diabetes and methylguanidine (mg) on GFR*

|  | (n) | per whole kidney | per g kidney |
|---|---|---|---|
| control | (10) | 1.33 ± 0.19 | 0.85 ± 0.07 |
| control + mg | (8) | 1.53 ± 0.29 | 0.87 ± 0.08 |
| diabetic | (10) | 1.81 ± 0.25$^a$ | 0.92 ± 0.14 |
| diabetic + mg | (9) | 1.59 ± 0.15$^{b,c}$ | 0.85 ± 0.09 |

*ml/min; values are mean ± 1SD measured using radiolabeled $^{57}$Co-EDTA
Significantly different from controls by Students' t-test: $^ap < 0.001$; $^bp < 0.005$
Significantly different from diabetics by Students' t-test: $^cp < 0.05$

TABLE 5

Effects of diabetes and methylguanidine (mg) on tissue sorbitol and myo-inositol

|  | control | control + mg | diabetic | diabetic + mg |
|---|---|---|---|---|
| number of rats | 7 | 8 | 11 | 9 |
| retina | | | | |
| sorbitol | 102 ± 16$^a$ | 102 ± 31 | 933 ± 275 | 533 ± 265 |
| myo-inositol | 1613 ± 516 | 1529 ± 187 | 1564 ± 452 | 1513 ± 402 |
| sciatic nerve | | | | |
| sorbitol | 183 ± 41 | 194 ± 75 | 1999 ± 334 | 1234 ± 710 |
| myo-inositol | 3943 ± 526 | 4263 ± 1587 | 3444 ± 639 | 3308 ± 792 |
| erythro- | | | | |

TABLE 5-continued

| | Effects of diabetes and methylguanidine (mg) on tissue sorbitol and myo-inositol | | | |
|---|---|---|---|---|
| | control | control + mg | diabetic | diabetic + mg |
| cytes | | | | |
| sorbitol | 6 ± 1 | 6 ± 2 | 44 ± 9 | 40 ± 8 |
| myo-inositol | 131 ± 47 | 104 ± 19 | 109 ± 20 | 103 ± 19 |

$^a$values are mean ± SD; see Methods in EXAMPLE I for test procedures

The methylguanidine and dimethylguanidine inhibitors of nitric oxide formation described herein can be used for administration to warm blooded mammals by conventional means, preferably in formulations with pharmaceutically acceptable diluents and carriers. The amount of the active inhibitor to be administered must be an effective amount, that is, an amount which is medically beneficial but does not present toxic effects which overweigh the advantages which accompany its use. It would be expected that the adult human daily dosage would normally range upward from about one milligram per kilo of body weight of the drug. A suitable route of administration is orally in the form of capsules, tablets, syrups, elixirs and the like, although parenteral administration also can be used, e.g. intraveneously, intraperitoneally or subcutaneously. Intravenous administration of the drug in aqueous solution such as physiologic saline is illustrative. Appropriate formulations of the drug in pharmaceutically acceptable diluents and carriers in therapeutic dosage form can be prepared by reference to general texts in the field such as, for example, *Remington's Pharmaceutical Sciences*, Ed. Arthur Osol. 16th ed., 1980, Mack Publishing Co., Easton, PA.

Various other examples will be apparent to the person skilled in the art after reading the present disclosure without departing from the spirit and scope of the invention. It is intended that all such examples be included within the scope of the appended claims.

References cited in parenthesis in the disclosure are appended hereto as follows:
1. D. J. Stuehr, H. J. Cho, N. S. Kwon, M. F. Weise, C. F. Nathan, *Proc. Natl. Acad. Sci. USA* 88, 7773 (1991).
2. S. Moncada, R. M. J. Palmer, E. A. Higgs, *Pharmacol. Reviews* 43, 109 (1991).
3. J. Garthwaite, Trends Neurol. Sci. 14:60 (1991).
4. J. B. Hibbs, Jr., et al., in *Nitric Oxide from L-Aroinine: a Bioregulatory System*, S. Moncada and E. Higgs, Eds. Elsevier, New York, (1990) pp 189-223.
5. G. Pugliese, R. G. Tilton, J. R. Williamson, *Diabetes/Metabolism Reviews* 7, 35 (1991).
6. C. Southern, D. Schulster, I. C. Green, *Febs Lett.* 276, 42 (1990).
7. J. A. Corbett, J. L. Wang, M. A. Sweetland, J. R. Lancaster, Jr., M. L. McDaniel, *Biochemical J.* (submitted).
8. J. A. Corbett, J. R. Lancaster, Jr., M. A. Sweetland, M. L. McDaniel, *J. Biol. Chem.* 266, 21351-21354 (1991).
9. J. R. Williamson et al., *Diabete & Metab.* 16, 3369 (1990). T. Soulis-Liparota, M. Cooper, D. Papazoglou, B. Clarke, G. Jerums, Diabetes 40, 1328 (1991).
10. M. Kihara et al., *Proc. Natl. Acad. Sci. USA* 88, 6107 (1991).
11. M. Brownlee, A. Cerami, H. Vlassara, *N. Engl. J. Med.* 318, 1315 (1988). M. Brownlee, H. Vlassara, A. Kooney, P. Ulrich, A. Cerami, *Science* 232, 1629 (1986).
12. R. Bucala, K. J. Tracey, A. Cerami, *J. Clin. Invest.* 87, 432 (1991).
13. L. C. Green et al., *Anal. Biochem.* 126, 131 (1982).
14. O. H. Lowry, J. V. Passoneau (1972) A Flexible System of Enzymatic Analysis. Orlando: Academis Press.
15. R.G. Tilton, K. Chang, G. Pugliese, D. M. Eades, M.A. Province, W. R. Sherman, C. Kilo, J. R. Williamson, *Diabetes* 38, 1258-1270 (1989).
16. G. Pugliese, R. G. Tilton, A. Speedy, K. Chang, M. A. Province, C. Kilo, J. R. Williamson, *Metabolism* 39, 690-697 (1990).
17. G. Pugliese, R. G. Tilton, K. Chang, A. Speedy, M. Province, D. M. Eades, P. E. Lacy, C. Kilo, J. R. Williamson, *Diabetes* 39, 323-332 (1990).
18. Y. Ido, R. G. Tilton, K. Chang, and J. R. Williamson, *Kidney Int.*, In press, 1992.
19. G. Pugliese, R. G. Tilton, A. Speedy, E. Santarelli, D. M. Eades, M. A. Province, C. Kilo, W. R. Sherman, J. R. Williamson, *Diabetes* 39 312-322 (1990).
20. M. J. Fregly, J. Lab. Clin. Med. 62, 223-230 (1963).
21. J. M. Pfeffer, M. A. Pfeffer, E. D. Frohlich, *J. Lab. Clin. Med.* 78, 957-962 (1997 ).

What is claimed is:
1. A method of inhibiting nitric oxide production in a warm blooded mammal diagnosed as being susceptible to diabetes-induced vascular dysfunction and complications which comprises administering to said mammal a nitric oxide inhibitory effective amount of methylguanidine or dimethylguanidine.
2. The method of claim 1 in which the methylguanidine or dimethylguanidine is administered to the mammal intravenously or subcutaneously.
3. The method of claim 1 in which the methylguanidine or dimethylguanidine is administered to a mammal at doses which inhibit nitric oxide production without substantially preventing formation of glucoseinduced, advanced glycation end products.
4. The method of claim 1 in which methylguanidine is administered to the mammal.
5. The method of claim 1 in which dimethylguanidine is administered to the mammal.

* * * * *